(12) United States Patent
Goldshtein

(10) Patent No.: US 6,878,693 B2
(45) Date of Patent: Apr. 12, 2005

(54) HYDROPHILIC COMPLEXES OF LIPOPHILIC MATERIALS AND AN APPARATUS AND METHOD FOR THEIR PRODUCTION

(75) Inventor: Rina Goldshtein, Har Hebron (IL)

(73) Assignee: SoluBest Ltd., Ness Ziona (IL)

( * ) Notice: Subject to any disclaimer, the term of this patent is extended or adjusted under 35 U.S.C. 154(b) by 31 days.

(21) Appl. No.: 09/966,847

(22) Filed: Sep. 28, 2001

(65) Prior Publication Data

US 2003/0064924 A1 Apr. 3, 2003

(51) Int. Cl.$^7$ ........................ A01N 43/04; A61K 31/715
(52) U.S. Cl. ............................ 514/54; 514/42; 514/43; 514/57; 424/489; 424/499; 424/500; 424/501; 536/22.1; 536/123; 536/124
(58) Field of Search ........................... 514/42, 43, 54, 514/57; 424/489, 499, 500, 501; 536/22.1, 123, 124, 1.11, 4.1, 18.7, 123.1; 422/209

(56) References Cited

U.S. PATENT DOCUMENTS

| | | | |
|---|---|---|---|
| 5,145,684 A | * 9/1992 | Liversidge et al. | 424/489 |
| 5,589,194 A | 12/1996 | Tsuei et al. | 424/497 |
| 5,629,021 A | 5/1997 | Wright | 424/489 |
| 5,693,608 A | 12/1997 | Bechgaard et al. | 514/2 |
| 5,734,071 A | 3/1998 | Fex et al. | 554/186 |
| 5,760,015 A | 6/1998 | Joullié et al. | 514/58 |
| 5,766,635 A | 6/1998 | Spenleuhauer et al. | 424/489 |
| 5,817,332 A | 10/1998 | Urtti et al. | 424/449 |
| 5,854,226 A | 12/1998 | Penkler et al. | 514/58 |
| 5,921,478 A | * 7/1999 | Kamiwano et al. | 241/5 |
| 6,015,574 A | 1/2000 | Cannell et al. | 424/450 |
| 6,120,794 A | 9/2000 | Liu et al. | 424/450 |
| 6,143,321 A | 11/2000 | Needham et al. | 424/450 |
| 6,197,757 B1 | 3/2001 | Perrier et al. | 541/53 |
| 6,207,180 B1 | 3/2001 | Ottoboni et al. | 424/426 |
| 6,217,886 B1 | 4/2001 | Önyuksel et al. | 424/401 |
| 6,221,389 B1 | 4/2001 | Cannell et al. | 424/450 |
| 6,221,399 B1 | * 4/2001 | Rolfes et al. | 424/489 |
| 6,224,794 B1 | 5/2001 | Amsden et al. | 264/4.1 |
| 6,225,063 B1 | 5/2001 | Khvorova et al. | 435/6 |
| 6,228,399 B1 | * 5/2001 | Parikh et al. | 424/489 |

FOREIGN PATENT DOCUMENTS

| | | |
|---|---|---|
| EP | 1 127 570 A2 | 8/2001 |
| WO | WO 97/04756 | 2/1997 |
| WO | WO 97/10849 | 3/1997 |
| WO | WO 00/74658 A1 | 12/2000 |

OTHER PUBLICATIONS

Akiyoshi, et al., "Hydrogel Nanoparticle Formed by Self-Assembly of Hydrophobized Polysaccharide. Stabilization of Adriamycin by Complexation", Eur. J. Pharm. Biopharm., 42(4):286–290 (1996).

Allémann, et al., "Drug–Loaded Nanoparticles—Preparation Methods and Drug Targeting Issues", Eur. J. Pharm. Biopharm., 39(5):173–191 (1993).

Chung, et al., "Thermo–Responsive Drug Delivery from Polymeric Micelles Constructed Using Block Copolymers of Poly(N–Isopropylacrylamide) and Poly(Butylmethacrylate", J. Controlled Release, 62(1–2):115–127 (1999).

Database WPI, Section Ch, Week 200041, Abstract, Derwent Publications Ltd., London, GB, Class A96, AN 1993–290554, XP–002248301 & Jp. 03 072340 B (Pola Chem. Ind. Inc.) Jul. 2000.

Jones, et al., "Polymeric Micelles—A New Generation of Colloidal Drug Carriers", Eur. J. Pharm. Biopharm., 48(2):101–111 (1999).

Jung, et al., "Sulfobutylated Poly(Vinyl Alcohol)–Graft–Poly(Lactide–co–Glycolide)s Facilitate the Preparation of Small Negatively Charged Biodegradable Nanospheres", J. Controlled Release, 67(2–3):157–169 (2000).

Kwon, et al., "Block Copolymer Micelles for Drug Delivery: Loading and Release of Doxorubicin", Journal of Controlled Release, 48(2–3):195–201 (1997).

Labhasetwar, et al., "Nanoparticles—A Colloidal Drug Delivery System for Primaquine and Metronidazole", J. Controlled Release, 12(2):113–119 (1990).

Pavanetoo, et al., "Evaluation of Process Parameters Involved in Chitosan Microsphere Preparation by the o/w/o Multiple Emulsion", J. Microencapsulation, 13(6):679–688 (1996).

Rolland, et al., "New Macromolecular Carriers for Drugs. I. Preparation and Characterization of Poly(Oxiethylene–b–Isoprene–b–Oxyethylene) Block Copolymer Aggregates", J. Applied Polymer Sci., 44(7):1195–1203 (1992).

Zhang, et al., "Increase in Gentamicin Uptake by Cultured Mouse Peritoneal Macrophages and Rat Hepatocytes by its Binding to Polybutylcyanoacrylate Manoparticles", Intl. J. Pharm., 164(1–2):21–27 (1998).

\* cited by examiner

Primary Examiner—James O. Wilson
Assistant Examiner—Patrick T. Lewis
(74) Attorney, Agent, or Firm—Browdy and Neimark, P.L.L.C.

(57) ABSTRACT

This invention provides a soluble inclusion complex formed of a water-insoluble lipophilic compound and an amphiphilic polymer and which demonstrated improved solubility and stability. The lipophilic compound within the inclusion complex may consist of pharmaceutical compounds, food additives, cosmetics, agricultural products and veterinary products. The invention also provides novel methods for preparing the inclusion complex, as well as a novel chemical reactor for forming the inclusion complex.

18 Claims, 1 Drawing Sheet

HYDROPHILIC COMPLEXES OF LIPOPHILIC MATERIALS AND AN APPARATUS AND METHOD FOR THEIR PRODUCTION

FIELD OF THE INVENTION

The invention is in the field of inclusion complexes. More particularly, the invention relates to inclusion complexes and methods of producing inclusion complexes that render insoluble compounds solubilized in water.

BACKGROUND OF THE INVENTION

Two formidable barriers to effective drug delivery and hence to disease treatment, are solubility and stability. To be absorbed in the human body, a compound has to be soluble in both water and fats (lipids). Solubility in water is, however, often associated with poor fat solubility and vice versa.

Over 40% of drug molecules and drug compounds are insoluble in the human body. In spite of this, lipophilic drug substances having low water solubility are a growing drug class having increasing applicability in a variety in a variety of therapeutic areas and for a variety of pathologies. There are over 2500 large lipophilic molecules in various stages of development today, and over 5500 small lipophilic molecules in development (See Drug Delivery Companies Report 2001, p.2, www.pharmaventures.com). Each of the existing companies has its own restriction and limitations with regard to both large and small molecules.

Solubility and stability issues are major formulation obstacles hindering the development of therapeutic agents. Aqueous solubility is a necessary but frequently elusive property for formulations of the complex organic structures found in pharmaceuticals. Traditional formulation systems for very insoluble drugs have involved a combination of organic solvents, surfactants and extreme pH conditions. These formulations are often irritating to the patient and may cause adverse reactions. At times, these methods are inadequate for solubilizing enough of a quantity of a drug for a parenteral formulation. In such cases, doctors may administer an "overdosage", such as for example with poorly soluble vitamins. In most cases, this overdosage does not cause any harm since the unabsorbed quantities exit the body with urine. Overdosage does, however waste a large amount of the active compound.

Although a number of solubilization technologies do exist, such as liposomes, cylcodextrins, microencapuslation, and dendrimers; each of these technologies have a number of significant disadvantages.

Phospholipids exposed to aqueous environment form a bi-layer structure called liposomes. Liposomes are microscopic spherical structures composed of phospholipids which were first discovered in the early 1960s (Bangham et al., J. Mol. Biol. 13: 238 (1965)). In aqueous media, phospholipid molecules, being amphiphilic, spontaneously organize themselves in self-closed bilayers as a result of hydrophilic and hydrophobic interactions. The resulting vesicles, referred to as liposomes, therefore encapsulate in the interior part of the aqueous medium in which they are suspended, a property that makes them potential carriers for biologically active hydrophilic molecules and drugs in vivo. Lipophilic agents may also be transported, embedded in the liposomal membrane. Liposomes resemble the bio-membranes and have been used for many years as a tool for solubilization of biological active molecules insoluble in water. They are non-toxic and biodegradable and can be used for specific target organs.

Liposome technology allows for the preparation of smaller to larger vesicles, using unilamillar (ULV) and multilamillar (MLV) vesicles. MLV are produced by mechanical agitation. Large ULV are prepared from MLV by extrusion under pressure through membranes of known pore size. The sizes are usually 200 nm or less in diameter, however, liposomes can be custom designed for almost any need by varying lipid content, surface change and method of preparation.

A number of companies such as Elan, Corp., Dublin, Ireland; Endorex Corp., Lake Forest, Ill.; Advanced Drug Deliveries Technologies, Muttenz, Switzerland; The Liposome Company, Inc., Princeton, N.J. (a subsidiary of Elan, Corp.); and Mibelle AG, Buchs, Switzerland, offer contract research and production facilities to the industry for the preparation of liposome inclusion complexes.

As drug carriers, liposomes have several potential advantages, including the ability to carry a significant amount of drug, relative ease of preparation, and low toxicity if natural lipids are used. However, common problems encountered with liposomes include: low stability, short shelf-life, poor tissue specificity, and toxicity with non-native lipids. Additionally, the uptake by phagocytic cells reduces circulation times. Furthermore, preparing liposome formulations that exhibit narrow size distribution has been formidable challenge under demanding conditions. Also, membrane clogging often results during the production of larger volumes required for pharmaceutical production of a particular drug.

Cyclodextrins are crystalline, water soluble, cyclic, non-reducing oligosaccharides built from six, seven, or eight glucopyranose units, referred to as alpha, beta and gamma cyclodextrin respectively, which have long been known as products that are capable of forming inclusion complexes. The cyclodextrin structure provides a molecule shaped like a segment of a hollow cone with an exterior hydrophilic surface and interior hydrophobic cavity.

The hydrophilic surface generates good water solubility for the cyclodextrin and the hydrophobic cavity provides a favorable environment in which enclose, envelope or entrap the drug molecule. This association isolates the drug from the aqueous solvent and may increase the drug's water solubility and stability. For a long time most cyclodextrins had been no more than scientific curiosities due to their limited availability and high price.

As a result of intensive research and advances in enzyme technology, cyclodextrins and their chemically modified derivatives are now available commercially, generating a new technology: packing on the molecular level. Companies such as Cyclolab Ltd., Budapest, Hungary; Cydex, Inc., Overland Park, Kans.; and Cyclops, Inc., Reykjavik, Iceland, have been involved in the development and manufacture of cyclodextrins.

Cyclodextrins are, however, fraught with disadvantages. An ideal cyclodextrin would exhibit both oral and systemic safety. It would have water solubility greater than the parent cyclodextrins yet retain or surpass their complexation characteristics. The disadvantages of the cyclodextrins include: limited space available for the active molecule to be entrapped inside the core, lack of pure stability of the complex, limited availability in the marketplace, and high price.

Microencapsulation is a process by which tiny parcels of a gas, liquid, or solid active ingredient are packaged within a second material for the purpose of shielding the active ingredient from the surrounding environment. These capsules, which range in size from one micron (one-thousandth of a millimeter) to approximately seven millimeters, release their contents at a later time by means appropriate to the application.

There are four typical mechanisms by which the core material is released from a microcapsule: (1) mechanical rupture of the capsule wall, (2) dissolution of the wall, (3) melting of the wall, and (4) diffusion through the wall. Less common release mechanisms include ablation (slow erosion of the shell) and biodegradation.

Microencapsulation covers several technologies, where a certain material is coated to obtain a micro-package of the active compound. The coating is performed to stabilize the material, cover for bad taste, preparing free flowing material of otherwise clogging agents etc. and many other purposes. This technology has been successfully applied in the feed-addition industry and to agriculture. The relatively high production cost needed for many of the formulations is, however, a significant disadvantage.

Dendrimers are a class of polymers distinguished by their highly branched, tree-like structures. They are synthesized in an iterative fashion from ABn monomers, with each iteration adding a layer or "generation" to the growing polymer. Dendrimers of up to ten generations have been synthesized with molecular weights in excess of 106 kDa. One important feature of dendrimeric polymers is their narrow molecular weight distributions. Indeed, depending on the synthetic strategy used, dendrimers with molecular weights in excess of 20 kDa can be made as single compounds.

Dendrimers, like liposomes, display the property of encapsulation, being able to sequester molecules within the interior spaces. Because they are single molecules, not assemblies, drug-dendrimer complexes are expected to be significantly more stable than liposomal drugs. Dendrimers are thus considered as one of the most promising vesicles for drug delivering systems. However, dendrimer technology is still in the research stage, and it is speculated that it will take years before the industry will apply this technology as a safe and efficient drug delivery system.

SUMMARY OF THE INVENTION

Lipophilic compounds that are solubilized in the form of inclusion complexes can be used in pharmacology, in the production of food additives, cosmetics, and agriculture, as well as in pet foods and veterinary products, amongst other uses.

The present invention provides inclusion complexes and methods for the production of inclusion complexes of water-insoluble lipophilic organic materials. The present invention also provides an apparatus for producing the inclusion complexes using the novel method of production.

The inclusion complex of the present invention is differentiated by the use of water soluble amphiphilic polymers that are capable of producing molecular complexes with lipophilic compounds or molecules. The inclusion complex formed in accordance with the present invention renders insoluble compounds soluble in water and readily bioavailable in the human body.

In accordance with the present invention, the inclusion complex is comprised of polymers with the lipophilic drug compound surrounded by and entrapped within the polymer. The inclusion complex involves the lipophilic compound or molecule, which is linked with the polymer by non-valence bonds and included into polymer-lipophilic over-molecular structure. The outer surface of the inclusion complex is comprised of a polymer that carries the drug molecule to the target destination. The inclusion complex may be nano-level in size, and no change occurs in the drug molecule itself when it is enveloped by the polymer. The inclusion complex remains stable for long periods of time, may be manufactured at a low cost, and may, in some cases, improve the activity of the drug.

The polymer of the inclusion complex is selected from the group amphiphilic polymers that demonstrate hydrophilic-lipophilic balance (HLB) so that the summary HLB of the inclusion complex produces water solubility with stable solutions of nano-emulsions. The amphiphilic polymer is selected using an algorithm that takes into account the molecular weight, the dimensions (in three directions) and the solubility in non-aqueous solvents of the lipophilic compound.

Unlike prior art inclusion complexes, the inclusion complex of the present invention imposes no limitations upon the size of the lipophilic compound that can be used. The conditions during the process of forming the inclusion complex are such that they do not lead to the destruction of the molecular composition of the lipophilic compound or to the loss of its physiological or biological activity. With regard to the process of preparing the inclusion complexes of the present invention, the process temperature is always lower than the temperature at which the lipophilic compound is losing its physiological or biological activity, or the temperature at which the lipophilic composition changes its chemical composition.

Depending upon the polymer used in the formation of the inclusion complex, drugs and pharmaceuticals within the complex are able to reach specific areas of the body readily and quickly. The polymer and lipophilic compound selected will also provide an inclusion complex capable of multi-level, multi-stage and/or controlled release of the drug or pharmaceutical within the body.

A significant advantage and unique feature of the inclusion complex of present invention is that no new bonds are formed and no existing bonds are destroyed during the formation of the inclusion complex. Additionally, existing conditions during the addition of the lipophilic compound into the formulation of the inclusion complex assures the creation of nano-particle. Furthermore, the ingredients used in the preparation of the inclusion complex are inexpensive, abundant, non-toxic and safe for use in the surrounding environment.

In another aspect of the present invention, a novel chemical reactor is provided for carrying out the method of the present invention. The chemical reactor of the present invention provides for continuous circulation of a "carrier" between the polymer solution and the lipophilic compound during the production of the inclusion complex of the present invention. This ensures a high uniformity of the emulsion formed during the process. The design of the chemical reactor allows all of the processes to occur in the same vessel, thus ensuring high purity in the final product and also simplifying the process and reducing the labor required.

The above description sets forth rather broadly the more important features of the present invention in order that the detailed description thereof that follows may be better understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

The invention will be better understood by reference to the appended figures in which.

DETAILED DESCRIPTION OF THE INVENTION

Figure 1:
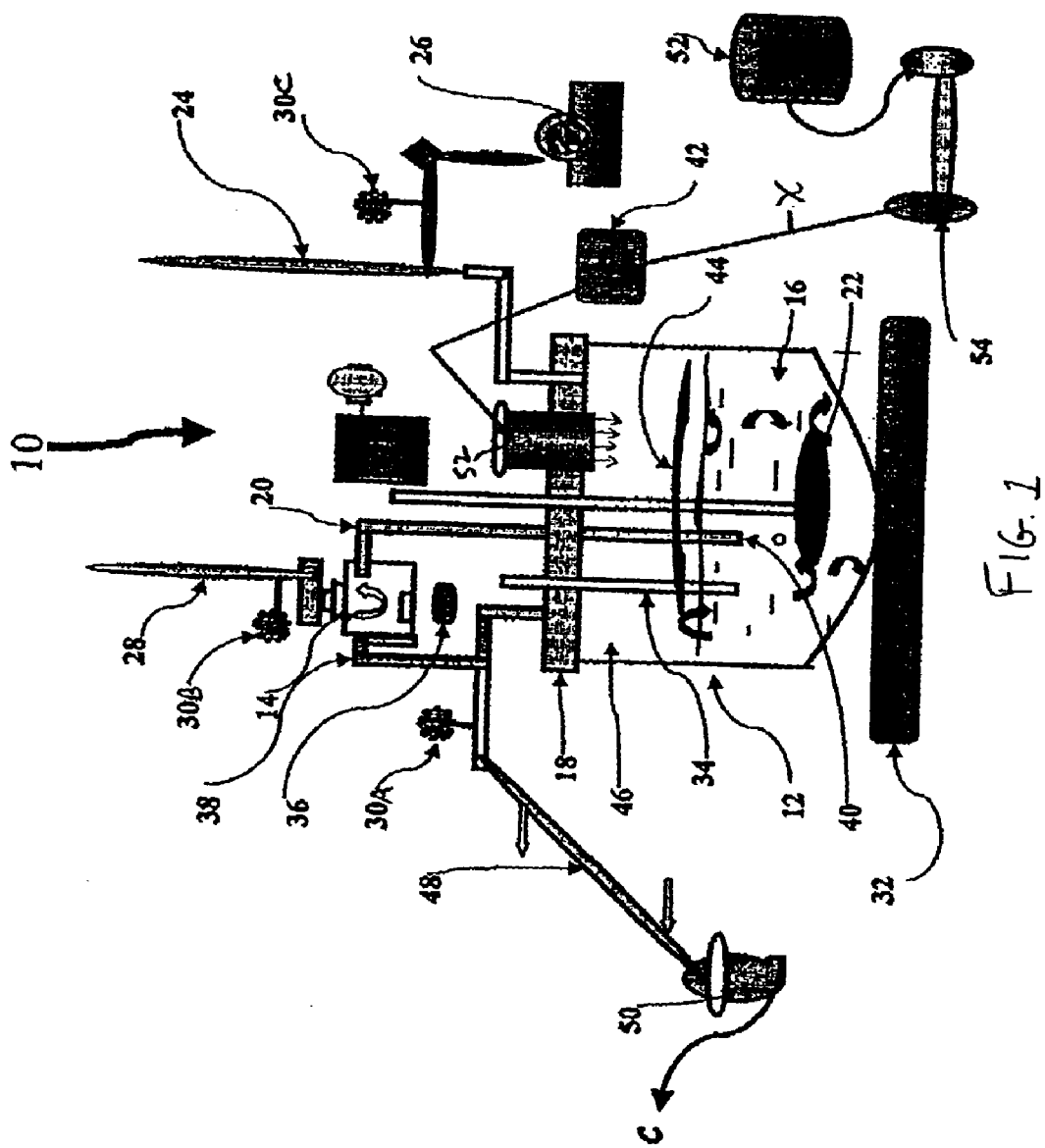
FIG. 1 is a schematic drawing of a chemical reactor for the manufacture of inclusion complexes in accordance with the present invention.

The inclusion complex of the present invention comprises an insoluble lipophilic compound entrapped within a water-soluble polymer. A variety of different polymers can be used for any selected lipophil or lipophilic compound. The polymer, or groups of polymers, is selected according to an algorithm that takes into account various physical properties of both the lipophilic compound and the interaction of the lipophilic compound within the resulting lipophil/polymer inclusion complex.

As used herein, the terms "lipophil", "lipophilic molecule" and "lipophilic compound" are used interchangeably and are all intended to refer to the same thing. The molecules and compounds referred to herein as lipophilic molecules and lipophilic compounds have a hydrophilic-lipophilic balance (HLB) of less than 6, and which fall within the HLB International scale, which ranges from 0–20. HLB is discussed in greater detail herein below.

More particularly, the ingredients of the composition of the present invention comprise the lipophilic compound and the polymer-complex creator. The lipophil may be any organic molecule or compound that is insoluble in the water and is preferably a drug or pharmaceutical composition. The lipophilic compound can be small or large, simple or complex, heavy or light and may comprise a variety of functional groups. The polymer or polymers used to make up the complex may be selected from the group of polymers approved for human use. Such polymers comprise, for example, but are not limited to: natural polysaccharides, polyacrylic acid and its derivatives, polyethylene imine and its derivatives, polymethacrylic acid and its derivatives, polyethylene oxide and its derivatives, polyvinyl alcohol and its derivatives, polyacetylene derivatives, polyisoprene derivatives and polybutadiene derivatives.

The polymer or groups of polymers used in the formation of the inclusion complex of the present invention are selected according to an algorithm that takes into account various physical properties of the lipophilic compounds and the polymer or polymers, as well as their future interaction in the resulting complex. The algorithm is utilized in this manner to select the optimal polymer(s) assesses properties such as pH, ionic force, temperature and various solvent parameters. More specifically, the amphiphilic polymer is selected using the algorithm that assesses the molecular weight, dimensions (in three directions) and the solubility of the lipophilic compound in non-aqueous solvents. The algorithm also takes into consideration the following properties of the polymer itself in selecting a polymer for the lipophil/polymer interaction in the formation of the inclusion complex: molecular weight, basic polymer chain length, the length of the kinetic unit, the solubility of the polymer in water, the overall degree of solubility, the degree of polymer flexibility, the hydrophilic-lipophilic balance, and the polarity of the hydrophilic groups of the polymer.

The polymer-complex creator comprises a selected polymer that is soluble in water, and has a hydrophilic-lipophilic balance (HLB) that assures solubility of the complex including the lipophil and the polymer. The carrier is a non-aqueous solvent of the water-insoluble lipophilic compound. The carrier is comprised of the lipophil solvent having a boiling point temperature lower than that of water (at that pressure at which the process of complex creation is being carried out). The creation of the inclusion complex does not involve the formation of any valent bonds (which may change the characteristics or properties of the lipophil). In the inclusion complex of the present invention, weak, non-covalent bonds, such as H-bonds and Van der Waals forces form during the creation of the inclusion complex. The formation of non-valent bonds preserves the structure and properties of the lipophilic compound, which is particularly important when the lipophilic compound is a pharmaceutical. As used herein, "non-valent" is intended to refer to non-covalent, non-ionic and non-semi-polaric bonds and/or interactions.

Following the selection of the lipophil and a determination is made of its requisite properties for construction of a geometrical model. A polymer suitable for complex inclusion complex with the given lipophilic compound is then selected. The main properties of the polymer include its HLB (hydrophilic-lipophilic balance) and the length and the flexibility of its polymer chain. The HLB of the polymer is selected in such a way that after combining to it the lipophilic compound the summary HLB of the inclusion complex renders the complex soluble. At this stage a geometrical model of the complex is constructed and determination is made of the length of the fragment of the polymer chain needed for inclusion complex. The HLB is calculated following the building of a virtual inclusion complex on a computer screen. The HLB can be calculated as a ration of hydrophilic and lipophilic groups on the surface of the virtual complex. The molecular weight of the complex is easily computed and its geometry is determined. More precisely, summary HLB of the inclusion complex in accordance with the present invention can be calculated after the virtual construction of the complex on the computer screen of a computer system upon which the aforementioned algorithm has been loaded as software. The algorithm that determines the summary HLB thus plays a major role in the selection of components from which the inclusion complex is formed. The parameters and library information pertaining to lipophilic compounds and polymer molecules are stored in the computer program for calculation of the summary HLB of the complex to be formed.

A determination of the weight correlation of the "amphiphilic polymer to lipophil" is then made. This determination is essential to the generation of the geometric model. The correlation is made based on the total length of the polymer chain, length of the fragment needed to create the complex, molecular mass of the lipophil and molecular mass of the fragment:

Formula:

$$N_c = \frac{M_f \times N_f}{M_l} = \frac{M_f}{M_l} \times \frac{M_p}{M_f} = \frac{M_p(\text{g-mol})}{M_l(\text{g-mol})}$$

wherein:

$N_c$—the weight ratio of the "amphiphilic polymer to lipophilic compound".

$M_f$—the molecular mass of the polymer fragment.

$M_l$—molecular mass of the lipophilic compound.

$M_p$—molecular mass of the polymer.

$N_f$—the quantity of the polymer fragments capable of participating in the complex creation.

Next, the physical parameters of the water solvent for the polymer are evaluated. At this stage determination is made of the pH required to create the complex, the necessary ionic force and the required carrier for the lipophilic compound. Use of the above components creates optimal conditions for controlling the flexibility of the polymer chain.

The carrier non-aqueous solvent is then selected. The purpose of this solvent to transfer the lipophil into a very weak (low concentration) solution such that the molecules of the dissolved lipophil practically do not react with one another. This solution is then delivered into the zone of reaction in the chemical reactor (discussed in detail herein below) for the creation of a nano-emulsion.

Unlike other known processes for the preparation of inclusion complexes where polymers are used for stabilization of the emulsion formed, only some of the amphiphilic polymers with previously calculated hydrophilic-lipophilic balance (HLB) are used.

Additionally, specific conditions are selected for the dynamic geometric conditioning of the amphiphilic polymer in the emulsion, which serves as the creator of the complex, as opposed to a viscosificator (increasing the viscosity). Previously calculated HLB provides for the necessary solubilization of the lipophilic compound.

Specific conditions created for the amphiphilic polymer in the nano-emulsion formation, results in two factors, the provision of free rotation of the kinetic segments of the polymer chain around the chemical bonds, thus connecting these segments, and the provision of non-valent interaction of the lipophilic functional groups of the amphiphilic polymer and the lipophilic groups of the compound intended for solubilization. These specific conditions include: the pH parameter of the dispersive medium, the ionic forces of the dispersive medium, the components composition of the dispersive medium, the temperature of the complex formulation, the process duration, and the mechanical components of the process. Each of these specific conditions will be discussed in more detail below.

The pH Parameter of the Dispersion Medium.

If the composition of the amphiphilic polymer includes ionogenic functional groups, the polymer could be soluble or at a pH higher then iso-electric point (polyacids) or lower than iso-electric point (polybases) depending on the polarity of these groups. In both of these cases the iso-electric point could be determined with a high degree of accuracy on the curve of "viscosity of the polymer solution-pH of the polymer solution". These two types of polymers could participate in the complex creation only inside the pH range where their solutions are viscous liquids. For polymers with non-ionogenic functional groups, the clearly defined iso-electric point does not exist and for this reason these polymers could participate in the complex creation in a wide pH range.

Ionic Force of the Dispersive Medium.

Under the influence of ions of the water-soluble salts in the polymer solution, the geometry of the amphiphilic polymer chains. This factor is used for creation of stereo-specific conditions of non-covalent interaction between lipophilic groups of the polymer and the lipophil itself. Nonetheless, many polymers react so actively on the appearance of the (a "salting out" process of the polymer), that it is not always possible to utilize this factor in the reaction of complex creation.

Competition exists between the ions and the polymer for water molecules and the ions take water from the hydrate shells of the polymer. As a result of decreasing hydrate shell, the polymer coils to a globule. The greater the ionic activity, the greater the polymer coiling to the globule.

Components Composition of the Dispersive Medium.

With the help of the composition of the solvents it is possible to flexibly control the geometry of the macromolecules. However, for the purpose of solubility (solubilization) of pharmaceuticals, food additives and cosmetics compounds, only biologically safe solvents, such as glycerol, ethylene glycol and less often ethyl alcohol, iso-butanol and dimethylsulfoxide could be used. Additive solvents decrease the dissolving capacity of water. This is similar to salts addition, i.e. the uncoiled polymeric chain transforming to a loose or compact globule. Thus, options for this methods are limited.

Temperature of the Complex Formation.

With the changes of the temperature of the polymer solution, the hydration conditions of the polymer molecule and accordingly its configuration in the solution drastically changes. With the raising of the temperature, hydration shells surrounding the polymer molecule start to detach and the linear macromolecule starts to take on globular form. At the same time, the flexibility of the macromolecule increases. As a result, additional positive conditions for complex creation are created.

The Process Duration.

Because of the non-valent interaction during creation of the inclusion, the limiting phase of the process consists of the diffusion of the lipophilic compounds and macromolecules to each other, for each reaction system exists at a minimum time for complex creation. If less time is allowed, the system remains two-phased. This two-phased nano-emulsion is thermodynamically unstable. The subsequent step of evaporating the carrier leaves particles of the dispersed phase in sizes ranging from 10–100 nanometers. The polymer molecule in the polymer solution then covers and entraps the lipophilic compounds that had remained in the particles of the dispersed phase after evaporation of the carrier, thus forming the stable inclusion complex. The remaining carrier is then evacuated by vacuum evaporation.

The Mechanical Component of the Process.

Mixers, dispersers, homogenizers and other equipment provide maximum dispersing of the lipophil in the water-polymer solution and accelerate creation of emulsion with nano-dimension size in a dispersed phase. An advantageous and novel chemical reactor for forming the nano-emulsion and inclusion complex of the present invention is discussed in detail herein below.

The combined effect of the above conditions in specifically selected dimensions and proportions supply the necessary conditions for the complex creation of the dynamic geometry of the polymer molecule, the maximum dispersing of the lipophil and the optimal conditions for the non-valent interaction of the polymer and lipophilic compounds during complex formation.

As recited above, the preparation of the inclusion complex in accordance with the present invention requires a number of calculations and procedures to be performed before the process of preparing the inclusion complex may actually be commenced.

Some calculations and procedures, which are determined using an algorithm on a computer system, include:

a) calculating the composition and properties of the components for preparing the inclusion complex, which comprises a lipophilic compound, an amphiphilic polymer, and carrier solvent;

b) calculating the weight ratio of the amphiphilic polymer to the lipophilic compound;

c) evaluating the physical parameters of the water solvent for the amphiphilic polymer;

d) determining the proper non-aqueous solvent;

e) creating a geometric model of the inclusion complex. The algorithm is not limited to these calculations and may be programmed to make additional calculations and determinations as necessary depending upon the properties and characteristics of the inclusion complex to be made.

As recited, the production of the molecular complex consisting of a lipophilic compound and an amphiphilic polymer according to the present invention, requires the dispersal of the lipophilic compound to nano-particle size. The nano-sized particles assure an almost immediate interaction between the dispersed nano-sized particles of the lipophilic compound and the polymer molecules. In accordance with the process of the invention it is also necessary to prevent reverse aggregation (coacervation) of the lipophilic nano-particles, and to assure an immediate interaction between the dispersed nano-particles of the lipophilic compounds and the polymer molecules. This assures the formation of a stable inclusion complex. The size of the lipophilic compound is determined by constructing its geometrical model (taking into account length of the connections and angles between these connections), and thereafter transferring the compound into a sphere; diameter of this sphere is the deciding measuring size of the lipophil compound. There is a need to take into account that lipophils with long chain structures have as a rule assume a shape having a globular configuration.

In accordance with the present invention, during the process of forming the inclusion complex, a polymer is added to an aqueous solvent, preferably water, to form a polymer solution in a first vessel of a chemical reactor. Additionally, ingredients may be added to adjust the pH and ionic force level of this solution as needed based on the parameters determined via the algorithm used to select the lipophilic compound and polymer. A lipophilic compound is placed in a second vessel of the chemical reactor. The lipophilic compound may be of any size, dimension or weight, and may comprise any of a variety of functional groups. A solution of the insoluble lipophilic compound in a non-aqueous solvent is referred to as the "carrier". The velocity of pouring or adding the carrier to the polymer solution is regulated by one or more regulating taps, which ensure that the lipophil solution being added to the polymer solution has a concentration below 0.1%.

The lipophil solution is formed when the polymer solution is heated and steam from the heated polymer solution condenses and dissolves the lipophil, present in the second vessel. The lipophil solution (in carrier) is then mixed with the polymer solution to form a dispersed phase in emulsion. Within the chemical reactor, the emulsion is fed into an area of turbulence caused by a disperser (more precisely a nano-disperser) that causes the formation of nano-sized lipophil molecules within the emulsion. The area of turbulence is referred to as the "action zone" or the "zone of interaction". The emulsion being fed into the area of turbulence has a Reynolds number of Re>10,000. The emulsion thus becomes a "nano-emulsion" having lipophilic particles of approximately 10 microns in size. Within the nano-emulsion there exists a dispersion medium comprised of the polymer solution, and a dispersed phase comprising the solution of the lipophil in the carrier. This two-phased nano-emulsion is, however, unstable. Evaporating the carrier leaves particles of the dispersed phase in sizes ranging from 10–100 nanometers. The polymer molecule in the polymer solution then "covers" or encloses the lipophilic compounds that had remained in the particles of the dispersed phase after evaporation of the carrier, thus forming the stable inclusion complex. The remaining carrier is then evacuated by vacuum evaporation. As a result of the algorithm used to select the optimal lipophil and polymer for the formation of the emulsion and resulting inclusion complex, no free polymer generally remains after the evaporation of the carrier.

The invention further comprises a novel chemical reactor designed for the production of the inclusion complexes in accordance with the present invention. As illustrated in FIG. 1, the chemical reactor 10 comprises a first vessel 12 and a second vessel 14. In accordance with the present invention, a polymer solution 16 comprised of the selected polymer in water is prepared having a concentration, pH and ionic properties in accordance with previously determined parameters. Distilled water vessel 52 contains distilled water indicated by "W" and is positioned in cover 18. The distilled water in distilled water vessel 52 is transferred to a polymer vessel 54 to which an estimated quantity of the selected polymer is added. This polymer solution formed in polymer vessel 54 is transferred to first vessel 12 via the action of peristaltic pump 42 as indicated by directional arrow "X". Polymer solution 16 is added into first vessel 12 via anopening in cover 18 with the assistance of peristaltic pump 42. A non-aqueous solvent ("carrier") is added to the polymer solution 16 in first vessel 12.

The lipophilic compound is added to second vessel 14, which is connected to first vessel 12 via reverse tube 20 so as to permit fluid communication between second vessel 14 and first vessel 12. A nano-disperser 22 is positioned within first vessel 12 to create turbulence in the solution and to effect dispersal of the lipophilic solution (in the carrier) that enters first vessel 12 from second vessel 14 via reverse tube 20. The nano-disperser 22 creates nano-sized lipophilic particles within the polymer solution 16 in first vessel 12. The nano-disperser 22 is also commonly referred to as a dispergator or homogenizer. A first condenser 24 connected to a vacuum pump 26 extends into first vessel 12. A second condenser 28 is connected to second vessel 14. Taps 30A, 30B, 30C are provided at various locations on the chemical reactor to control first and second condensers 24, 28, as well as to regulate the flow of solutions and vapors between said first vessel 12 and said second vessel 14.

An electrical heater 32 is positioned below first vessel 12 to heat solution 16 therein. First vessel 12 is heated above the boiling point of the carrier, which is lower than the boiling point of polymer solution 16. An electric thermometer 34 extends into first vessel 12 to control and monitor the temperature of solution 16 within first vessel 12. A magnetic mixer and heater 36 is positioned below second vessel 14 to heat and mix the lipophilic compound with the carrier solvent in second vessel 14.

As a result of the heating, the vapors of the non-water solvent (carrier) in first vessel 12 rise up through a steam pipe 38, enter second vessel 14 and condense therein. In second vessel 14, the lipophilic compound slowly dissolves in the non-aqueous solvent and the resulting lipophilic solution flows via reverse tube 20 back into the first vessel 12. An opening 40 of reverse tube 20 is arranged in such a way that the lipophilic solution enters first vessel 12 in the area close to the nano-disperser 22, referred to as the "action zone" or "reaction zone", and has a turbulent flow with a Reynolds number of Re>10,000. The Reynolds number is a measurement of the smoothness of flow of a fluid. A high Reynolds number implies that the flow is turbulent, while a low Reynolds number implies that the flow is laminar. The emulsion is formed here. In the action zone, the nano-disperser operates in the range of approximately 5,000 to 10,000 revolutions per minute.

Screen 44 prevents this turbulent flow from entering the air space 46 of the first vessel 12 above the liquid phase. The process is continued until the entire lipophilic compound transfers into the polymer solution 16. The non-water solvent is removed from both vessels 12, 14 via cooler 48 into a condensate container 50. The removal of the non-water solvent is illustrated by the arrow indicated by the letter "C". The leftover non-aqueous solvent in first vessel 12 is removed with the assistance of vacuum pump 26.

Depending upon the previously determined protocol for a given reaction system regime, the temperature is then lowered to ambient while simultaneously reducing the rotation speed to zero.

Although the present invention has been described with reference to use in the human body, the invention is not limited in this respect and inclusion complexes can be formed in accordance with the present invention for use in veterinary pharmaceuticals and products as well.

EXAMPLES

Experimental Procedure for the Production of the Inclusion Complex

1. Preparation of Polymer Solution.

500 ml of distilled water are transferred from distilled water vessel 52 to polymer vessel 54. To polymer vessel 54 is added an estimated quantity of polymer, which was chosen for creation of Inclusion Complex with lipophilic compound. At temp. 20–25° C. the contents of polymer vessel 54 is mixed at velocity of 30–60 $min^{-1}$ (rotation/min). up to complete dissolution of the polymer and creation of transparent or opalescent solution.

2. Loading Compounds in the Reactor.

The polymer solution, prepared in polymer vessel 54 is transferred into first vessel 12 by pump 42. In the same vessel the carrier solvent is loaded. Lipophilic compound is placed into second vessel 14.

3. Starting the Reactor.

The nano-disperser 22 is activated at velocity 500–800 $min^{-1}$. The cooling water is entered into first and second condensers 24 and 28. The heater (thermostat) 32 is activated for temperature 5–10° C. above the boiling point of carrier solvent. The magnetic mixer 36 is activated at velocity 5–10 $min^{-1}$.

4. Synthesis of the Complex.

After reaching the designated temperature, the carrier solvent starts evaporation from first vessel 12. Its vapor reaches second vessel 14 through steam pipe 38. At this moment the nano-disperser 22 is accelerated to a velocity of 8,000–10,000 $min^{-1}$. The solution of lipophilic compound in the carrier solvent then moves from second vessel 14 to first vessel 12 through reverse tube 20. The solution exits through opening 40 and reaches to the zone of the most active action of nano-disperser 22. The temperature in the beater 32 is raised another 5–10° C. in order the concentration of lipophilic compound in the carrier solvent remained within the range 0.02–0.1%. The process lasts until all lipophilic compound passes from second vessel 14 to first vessel 12.

5. Removing the Carrier Solvent.

The velocity of the nano-disperser reduced to 200–300 $min^{-1}$. Tap 30A is opened on the conduit connecting first vessel 12 with cooler 48 and condensate container 50. The carrier solvent is distilled off to condensate container 50. After the solvent is transferred, tap 30A is closed together with tap 30B on cooler 28. Tap 30C, which is positioned on the conduit connecting first vessel 12 with vacuum-pump 26, is then opened. The temperature in the heater 32 is then reduced to 30–35° C., the vacuum-pump 26 is activated and the remnants of the solvent are evacuated for 1–2 hours. The vacuum-pump 26 is then deactivated, all taps 30A, 30B and 30C are opened and the velocity of the nano-disperser is reduced to 30–60 $min^{-1}$.

6. Completing the Experiment.

The solution of the inclusion complex is taken from first vessel 12 and is analyzed.

Combination of Water-phase, Polymer, and Lipophilic Drug Agent and the Process Temperature Used for the Preparation of Selected Nano-emulsions and their Stability (Pre-formulation Level) Determined via Length of Time (Days).

| Solvent (water phase) | Polymer | Carrier | Lipophilic drug agent | Process Temp (° C.) | Stability (days) |
|---|---|---|---|---|---|
| Water + 0.9% NaCl | Carragenan | Hexane | Vaseline(Oleum vaselini), hydrocarbons' mixture | 65 | 30 |
| Solvent "Quartasolum" (NaCl, KCl, $NaHCO_3$, $CH_3COONa$) | Xantan | Diethyl ether | Nut oil & almond oil (Oleum Amigdalarum) 1:1, aromatic esters' mixture, triglycerides, aromatic nitriles and vitamins | 60 | 300 |
| Distilled water + ethanol (10%) | Polyacryl-amide | Diethyl ether | Oregano oil, phenols and polyphenols, complicated aromatic esters' mixture | 55 | 100 |
| Distilled water + glycerol (10%) | Starch | Benzene | Simethicone, olygo(dimethylsiloxan)s mixture (Antifoaming medication) | 70 | 30 |
| Solvent "Quartasolum" | Agar-agar | Diethyl ether | Pine Oil (raw material for Camphora), mixture of camphora, turpentine and other terpens and terpenoids | 60 | 100 |

Equivalents

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is to be understood that the drawings are not necessarily drawn to scale, but that they are merely conceptual in nature.

What is claimed is:

1. A hydrophilic inclusion complex consisting essentially of nano-sized particles of a water-insoluble lipophilic compound surrounded by and entrapped within an amphiphilic polymer, wherein said inclusion complex renders said lipophilic compound soluble in water.

2. The hydrophilic inclusion complex as recited in claim 1, wherein said lipophilic compound is selected from the group consisting of pharmaceutical compounds, food, additives, cosmetics, agricultural products and pet foods.

3. The hydrophilic inclusion complex as recited in claim 2, wherein said lipophilic compound is selected from the group consisting of vitamins, antibiotics and hormones.

4. The hydrophilic inclusion complex as recited in claim 1, wherein said nano-sized particles of said lipophilic compound interact with said amphiphilic polymer via the formation of non-valent bonds.

5. The hydrophilic inclusion complex as recited in claim 1, wherein said amphiphilic polymer and said particles of said lipophilic compound form an inclusion complex having a hydrophilic-lipophilic balance that renders said inclusion complex soluble in water.

6. The hydrophilic inclusion complex as recited in claim 1, wherein said nano-sized particles of said water-insoluble lipophilic compound are in the range of from 10–100 nanometers in size.

7. A method for forming a hydrophilic inclusion complex consisting essentially of nano-sized particles of a water-insoluble lipophilic compound surrounded by and entrapped within an amphiphilic polymer, the method comprising adding a low concentration solution of said lipophilic compound in a non-aqueous solvent to a turbulent zone in an aqueous solution of said polymer heated to a temperature above the boiling point of said non-aqueous solvent, to form said hydrophilic inclusion complex, wherein said hydrophilic inclusion complex consists essentially of said nano-sized particles of said water-insoluble lipophilic compound surrounded by and entrapped within said amphiphilic polymer, and wherein said inclusion complex renders said lipophilic compound soluble in water.

8. The method as recited in claim 7, wherein said lipophilic compound is selected from the group consisting of vitamins, antibiotics and hormones.

9. The method as recited in claim 7, wherein said amphiphilic polymer comprises natural polysaccharides.

10. The method as recited in claim 7, wherein the remaining non-aqueous solvent after formation of the inclusion complex is evacuated by vacuum evaporation.

11. The process as recited in claim 7, wherein said lipophilic compound is an organic materials selected from the group consisting of drugs, food additives, cosmetics, agricultural products and pet foods.

12. The hydrophilic inclusion complex as recited in claim 1, wherein said amphiphilic polymer comprises natural polysaccharides.

13. The hydrophilic inclusion complex as recited in claim 1, wherein said hydrophilic inclusion complex is bioavailable.

14. The hydrophilic inclusion complex as recited in claim 2, wherein said lipophilic compound selected from the group consisting of peptides and polypeptides, nucleotides and co-ferments, vitamins, steroids, porphyrins, metal-complexes, purines, pyrimidines, antibiotics and hormones.

15. The method as recited in claim 7, wherein said lipophilic compound is selected from the group comprising of peptides and polypeptides, nucleotides and co-ferments, vitamins, steroids, porphyrins, metal-complexes, purines, pyrimidines, antibiotics and hormones.

16. The method as recited in claim 7, wherein said amphiphilic polymer is selected from the group consisting of natural polysaccharides, polyacrylic acid and its derivatives, polyethylene imine arid its derivatives, polymethacrylic acid and its derivatives, polyethylene oxide and its derivatives, polyvinyl alcohol and its derivatives, polyacetylene derivatives, polyisoprene derivatives and polybutadiene derivatives.

17. The method as recited in claim 7, wherein said hydrophilic inclusion complex is bioavailable.

18. The hydrophilic inclusion complex as recited in claim 13, wherein said lipophilic compound is a pharmaceutical compound.

* * * * *